United States Patent [19]

Stewart

[11] 4,096,749

[45] Jun. 27, 1978

[54] CORE SAMPLING DEVICE

[76] Inventor: Robert A. Stewart, 2844 54th St., North, St. Petersburg, Fla. 33710

[21] Appl. No.: 792,465

[22] Filed: Apr. 29, 1977

[51] Int. Cl.² .................... B28B 7/10; G01N 1/08
[52] U.S. Cl. ...................... 73/425.2; 249/DIG. 4
[58] Field of Search ............. 73/425.2, 425; 249/DIG. 4, 1; 52/705

[56] References Cited

U.S. PATENT DOCUMENTS

| 2,084,686 | 6/1937 | Howard | 73/425.2 X |
| 3,137,971 | 6/1964 | Rhodes | 52/705 X |
| 3,162,256 | 12/1964 | Meinecke | 73/425.2 X |
| 3,442,481 | 5/1969 | Di Stasio | 249/DIG. 4 |
| 3,461,192 | 8/1969 | Di Stasio | 249/DIG. 4 |
| 3,589,665 | 6/1971 | Onesti et al. | 249/DIG. 4 |
| 3,807,234 | 4/1974 | Duperon | 73/425.2 |

Primary Examiner—Daniel M. Yasich
Attorney, Agent, or Firm—Duckworth, Hobby, Allen & Pettis

[57] ABSTRACT

A core sampling device of the type utilized in forming concrete test cores in situ including a double-walled sleeve which is placed into the wet, fluid concrete in combination with an insertion tool whereby the sleeve, due to its configuration, may be pressed or "screwed" into the fluid concrete. By virtue of the double-walled construction of the sleeve, once the concrete has cured, the test core may be easily removed therefrom.

8 Claims, 7 Drawing Figures

CORE SAMPLING DEVICE

BACKGROUND OF THE INVENTION

1. Field of the Invention

The present invention relates to a core sampling device of the type primarily intended for forming concrete test cores in situ and facilitating the removal of such test cores. The core sampling device basically comprises a double-walled sleeve means in combination with insertion means removably engageable with the sleeve means to dispose the sleeve means in operative position within a wet, fluid concrete material. 2. Description of the Prior Art The use of concrete and similar cementitious material in the construction of buildings, roadways, runways and other such load-bearing structures is, of course, well known in today's industrialized world. However, in recognition of the fact that the load-bearing capabilities of concrete and other cementitious compositions are directly related to the formulation, mixing and curing of the materials, it has become common practice to utilize test cores of the material in order to verify that its load-bearing capabilities satisfy the specifications of the particular application. Accordingly, a number of techniques and devices are known in the prior art for forming and/or extracting such concrete test cores.

One common method of obtaining concrete test cores comprises the use of a hollow, cylindrical drill for boring and removing the test core once the concrete has cured. However, it can be appreciated that mechanically cutting and extracting a test core is not only time-consuming and expensive, but may actually damage surrounding material as the core is cut and removed. In recognition of these problems, devices in the nature of molds for casting test cores have been developed.

One such mold is disclosed in U.S. Pat. No. 3,163,908 to Lawmaster. That patent discloses a multi-part, reusable plastic mold for casting test cylinders of concrete, gypsum and like materials. Another mold construction is shown in U.S. Pat. No. 3,442,481 to Di Stasio. That Di Stasio patent teaches the use of separate inner and outer members having registering openings, whereby concrete may flow within the inner member, after which the opening in the inner member is closed and the concrete is permitted to set. Other exemplary mold devices are shown in U.S. Pat. Nos. 3,176,053 and 3,527,439.

While each of the above patents clearly disclose and teach apparatus which is useful for its intended purpose, it must be noted that each of the molds disclosed comprise a plurality of separate, distinct elements. Moreover, the construction of the molds generally requires some mechanical manipulation of at least one mold element so as to allow concrete to flow within the mold cavity. Once the mold has been filled with concrete, it is then generally necessary to again manipulate a mold element so as to seal the mold cavity from the surrounding fluid concrete. It should also be noted that many of the prior art devices require some external fastening means so as to secure the mold within the fluid concrete. Finally, some prior art molds are not intended for in situ testing at all, but are utilized simply as a "portable" container for a small quantity of the concrete.

Accordingly, it is apparent that there is a great need in the art for a core sampling device suitable for in situ use having virtually no moving parts and requiring no external fastening means for securing the core within the fresh concrete. Of course, such a core sampling device should be constructed so as to allow easy, rapid removement of the hardened test core without the necessity of utilizing any special core removal tool or device. Similarly, since such core sampling devices are normally considered an expendable item, the device must be of relatively simple, inexpensive construction. Finally, it is to be appreciated that a core sampling device suitable for use in situ will certainly provide test cores which are more truly representative of the structural capabilities of the material being tested.

SUMMARY OF THE INVENTION

The present invention relates to a core sampling device of the type primarily intended for forming concrete test cores in situ and facilitating the removal of those test cores. Basically, the core sampling device comprises a sleeve means which defines the configuration of the test core and an insertion means removably engageable with the sleeve means for dispostiion of the sleeve means within the fresh, fluid concrete. In the preferred embodiment, the sleeve means comprises a cylinder defined by first and second walls means. The first wall means defines a first cylinder, and the second wall means defines a second cylinder of relatively lesser diameter than that of the first wall means. Accordingly, the first wall means is disposed in surrounding, congruent relation to the second wall means. The first and second wall means are interconnected at their bases so as to define therebetween a void which is open at the top. The cylindrical volume within the second wall means defines the configuration of the test core, and this cylindrical volume is open at both the top and the bottom. For purposes of example only, the volume defining the test core is preferably 3 inches in diameter and 6 inches in height. Similarly, the void between the first and second wall means is in the order of ¼ inch.

The insertion means of the present invention comprises a body means dimensioned and configured for being removably disposed within the space or void defined between the first and second wall means. Attached to the top of the body means is suitable handle means whereby a mechanical force may be transferred from the body means to the sleeve means, thereby placing the sleeve means within the wet, fluid concrete. In the preferred embodiment, the handle means comprises a T-bar attached to the top of the body means by substantially radially extending reinforcing arms.

In order to facilitate the placement of the core sampling device within the fluid concrete, and to insure that the sleeve means of the core sampling device will not float, or rise from the fluid concrete, alternate embodiments of the device have been perfected. In one such alternate embodiment anti-float means are disposed on the exterior of the first wall means in engaging relation to the concrete from which the test core is being obtained. For example, this anti-float means may comprise a spiral flange defining at least one revolution about the exterior of the first wall means. This spiral flange may then be utilized to "screw" the sleeve means into the fluid concrete. The spiral flange will also serve to prevent the relatively light sleeve means from rising, or floating, out of the fluid concrete.

In yet another embodiment, a plurality of insertion ledge means are formed in interconnecting relation between the first and second wall means at their bases. Corresponding insertion finger means are formed around the peripheral edge of the insertion body means opposite from the insertion handle means. The finger means are dimensioned and configured to interlock the insertion ledge means so as to allow a twisting force to be transmitted from the handle means to the sleeve means, thereby facilitating insertion of the device into the fluid concrete.

In operation, once the concrete material has been poured and the locations for test cores determined, an insertion means is operatively disposed within the space defined by the first and second wall means of the device sleeve means. Then, utilizing the handle means, the sleeve means is operatively inserted into the fluid concrete. Inasmuch as the volume defined by the second wall means is open at the base, it is obvious that concrete will fill the test core void. The insertion means is then removed and utilized in combination with subsequent sleeve means for the placing of further test cores. Once the concrete has cured sufficiently so as to allow structural testing, the core may be removed in the following fashion. A screwdriver or similar bar-type device is inserted into the space defined by the first and second wall means. Then the screwdriver is simply forced against the second wall means, thereby causing the second wall means and the test core defined thereby to break or shear from the main body. The screwdriver and core may then be removed. If, due to sequential testing, it is determined that sufficient structural strength has been obtained before all test cores have been removed, they may simply be left in place, and the void between the first and second wall means may be filled with grout or any such suitable substance.

Finally, though not necessary to removal of the test core, it has been determined that it may be desirable to form the second wall means to include a weakened portion defining an annular segment adjacent the base of the second wall means. This would clearly facilitate breaking, or shearing, of the second wall means when removal of the test core was desired.

The invention accordingly comprises an article of manufacture possessing the features, properties and the relation of elements which will be exemplified in the article hereinafter described and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
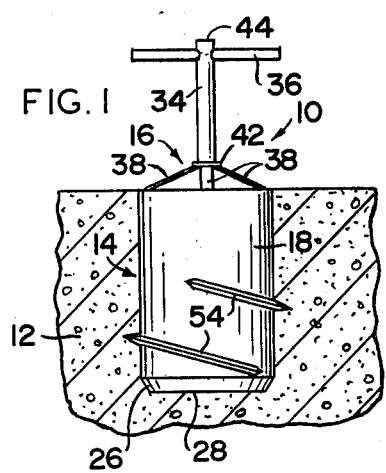
FIG. 1 is an elevational view showing the core sampling device of the present invention operatively disposed within a concrete structure.

The core sampling device of the present invention is generally indicated as 10, and is shown in the view of FIG. 1 operatively positioned within a fresh pour of concrete 12. As perhaps most clearly seen in the view of FIG. 2, core sampling device 10 basically comprises sleeve means generally indicated as 14 and insertion means generally indicated as 16, removably engageable with the sleeve means 14.

Sleeve means 14 comprises a first wall means 18 defining a substantially cylindrical configuration and second wall means 20 congruently disposed within first wall means 18. As best seen in the exploded view of FIG. 2, base 22 of first wall means 18 and base 24 of second wall means 20 are interconnected as by substantially triangular member 26, apex 28 of triangular member 26 extending downwardly. By virtue of this construction, a space 30 is defined between first wall means 18 and second wall means 20. Space 30 is closed at its point of intersection with interconnecting triangular member 26 and is open at the top of sleeve means 14 so that insertion means 16 may be placed therein.

Insertion means 16 comprises insertion body means 32 dimensioned and configured for being removably disposed within space 30 of sleeve means 14. Operatively attached to the top of body means 32 is an insertion handle means comprising central shaft 34, gripping arm 36 disposed at the top of shaft 34, and radially extending reinforcing arms 38 disposed in fixed, interconnecting relation between central shaft 34 and body means 32. As most clearly seen in the exploded view of FIG. 2, gripping arms 36 preferably comprise a cylindrical member attached to central shaft 34 by passing arms 36 through shaft aperture 40 formed in the top of central shaft 34. An enlarged surface 42 is provided on central shaft 34 for the purpose of facilitating the attachment of reinforcing arms 38 thereto in fixed relation between shaft 34 and body means 32. It should also be noted that a top segment 44 of central shaft 34 extends above arms 36 to provide a striking surface, as for a hammer, to assist in placing device 10 within the concrete 12.

Figure 3:
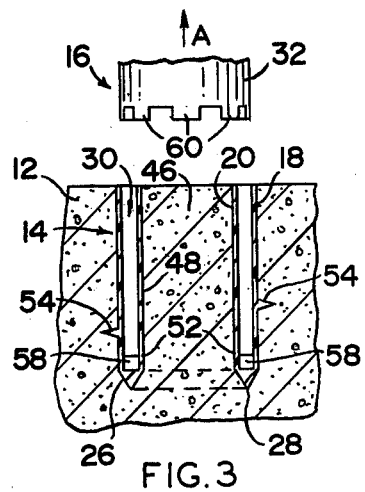
FIG. 3 is a sectional view illustrating the placement of the sleeve means within the concrete structure and removal of the insertion means therefrom.

By virtue of the construction thus far described, it can be seen that insertion means 16 may be placed within space 30 of sleeve means 14, and that gripping arms 36 may then be utilized to dispose device 10, and particularly sleeve means 14, within concrete 12. As sleeve means 14 is inserted into concrete 12, a quantity of concrete comprising the test core 46 will fill the substantially cylindrical void 48 defined by the interior of second wall means 20. Once sleeve means 14 has been operatively disposed within concrete 12, insertion means 16 may be removed as indicated by arrow A in the view of FIG. 3. Once the concrete 12 and test core 46 has cured sufficiently for testing, test core 46 is removed as illustrated in the views of FIGS. 4 and 5.

Figure 4:
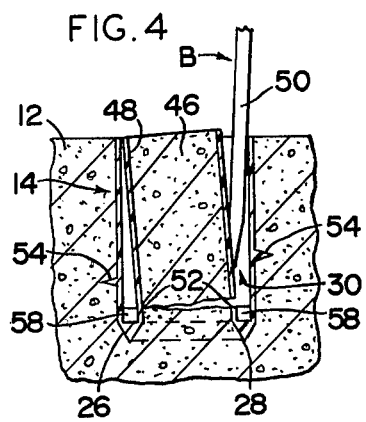
FIG. 4 is a sectional view illustrating shearing, or breaking, of the test core from the cement structure.
Figure 5:
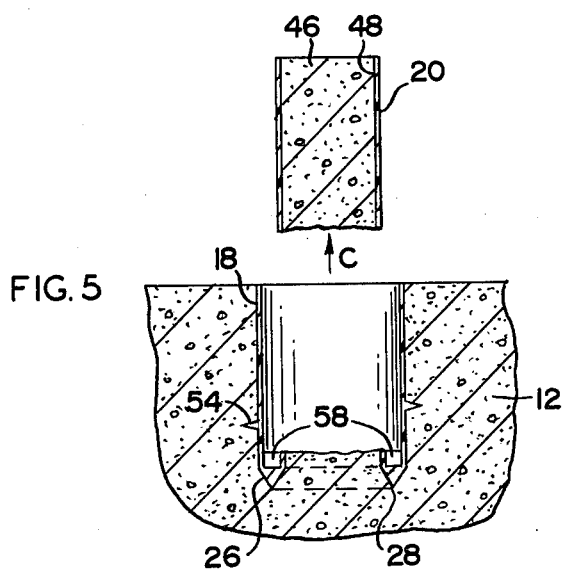
FIG. 5 is a sectional view illustrating removal of the test core from the sleeve means.
Figure 6:
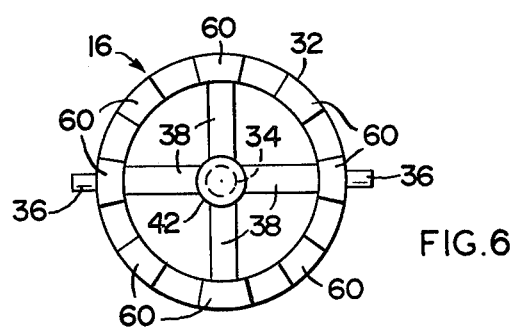
FIG. 6 is a plan view of the insertion means taken along line 6—6 of FIG. 2.
Figure 7:
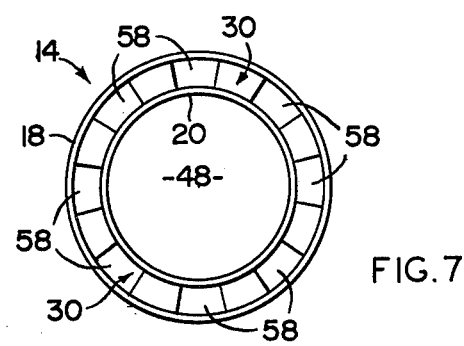
FIG. 7 is a sectional view of the sleeve means taken along line 7—7 of FIG. 2.

As best seen in the view of FIG. 4, an elongated, rigid member, such as, for example, screwdriver blade 50 is inserted into space 30 between first wall means 18 and second wall means 20. Screwdriver blade 50 is then forcibly tilted in the direction of arrow B thereby causing second wall means 20 and test core 46 to fracture and separate from sleeve means 14 and concrete 12, respectively. Then, as best seen in the view of FIG. 5, test core 46 and its surrounding second wall means 20 may be removed in the direction indicated by arrow C. In this regard, and for the specific purpose of assisting in the removal of test core 46 and second wall means 20, it should be noted tht second wall means 20 may be formed to include a weakened portion defining an annular segment 52 juxtaposed with interconnecting triangular member 26.

Figure 2:
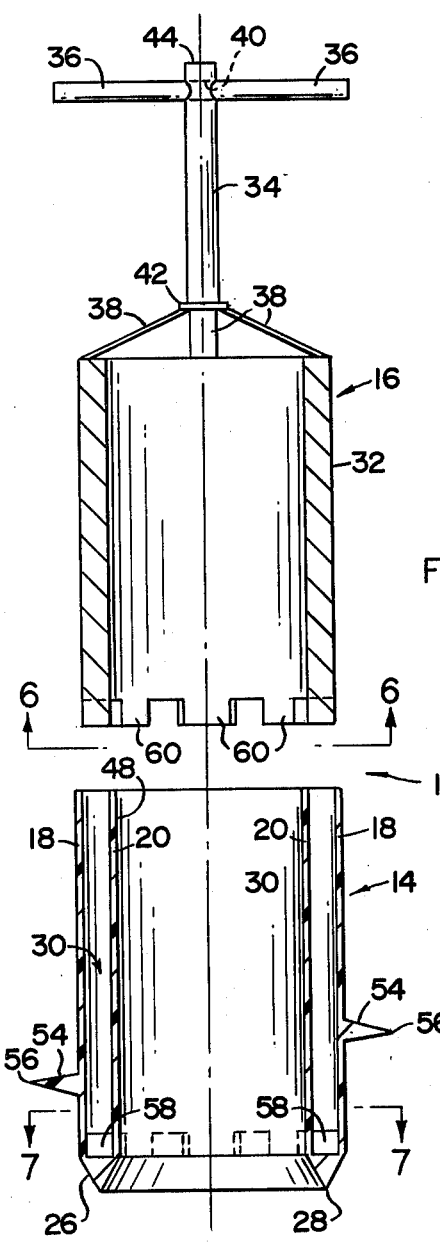
FIG. 2 is an exploded, sectional view showing the sleeve means and insertion means of the core sampling device.

The core sampling device 10 may further comprise anti-float means comprising a spiral flange 54 formed on the exterior of the first wall means 18. As best seen in the view of FIG. 2, spiral flange 54 includes an exposed edge 56 extending outwardly from first wall means 18 in substantially transverse relation thereto. Furthermore, as best seen in the view of FIG. 1, spiral flange 54 preferably completes slightly more than one revolution around first wall means 18. By virtue of this construction, edge 56 of flange 54 will "bite" into concrete 12, thereby preventing sleeve means 14 from rising, or floating, out of concrete 12. Of course, by virtue of the construction of flange 54 to define a spiral, the insertion of sleeve means 14 into concrete 12 may be accomplished as by "screwing" sleeve means 14 into concrete 12.

A further embodiment of device 10 includes modification of sleeve means 14 and insertion means 16 so as to increase the ease with which device 10 may be operatively disposed within concrete 12. More specifically, this embodiment comprises the formation of insertion ledge means 58 in interconnecting, spaced relation between first wall means 18 and second wall means 20. Correspondingly dimensioned and configured insertion finger means 60 are formed on the end of insertion body means 32 opposite from the insertion handle. When insertion means 16 is operatively disposed within sleeve means 14, insertion ledge means 58 and insertion finger means 60 intermesh, thereby allowing sleeve means 14 to rotate about its longitudinal axis as gripping arms 36 are twisted about the axis defined by central shaft 34. Thus, in effect, insertion means 16 will operatively engage sleeve means 14 to thread, or screw, sleeve means 14 into concrete 12 and thereby form a test core 46.

It will thus be seen that the objects set forth above, among those made apparent from the preceding description, are efficiently attained and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A core sampling device of the type primarily intended for forming concrete test cores in situ and facilitating the removal of such test cores, said core sampling device comprising: sleeve means comprising first wall means defining the exterior of said device and second wall means correspondingly configured as said first wall means and disposed within said first wall means, said first and second wall means being interconnected at their bases; a plurality of insertion ledge means formed in interconnecting relation between said first and second wall means bases; and insertion means removably engageable with said sleeve means, said insertion means comprising body means dimensioned and configured for being removably disposed within the space defined between said first and second wall means, said insertion means further comprising a plurality of insertion finger means formed around a peripheral edge of said body means, said finger means being dimensioned and configured to operatively engage said insertion ledge means, whereby said insertion means may be utilized to place said sleeve means within fluid concrete to form a test core at least partially defined by said second wall means.

2. A core sampling device as in claim 1 wherein said first and second wall means are cylindrical, the diameter of said first wall means being relatively greater than the diameter of said second wall means.

3. A core sampling device as in claim 1 wherein said interconnection between said first and second wall means bases defines a substantially triangular cross-section, the apex of said cross-section extending downwardly, away from said first and second wall means.

4. A core sampling device as in claim 1 further comprising anti-float means disposed on the exterior of said first wall means, whereby said sleeve means is held within the fluid concrete.

5. A core sampling device as in claim 4 wherein said anti-float means comprises flange means, an exposed edge of said flange means extending outwardly from said first wall means exterior.

6. A core sampling device as in claim 5 wherein said flange means comprises a spiral flange defining at least one revolution about said first wall means exterior.

7. A core sampling device as in claim 1 wherein said insertion means further comprises handle means operatively disposed at one end of said body means.

8. A core sampling device as in claim 1 further comprising core removal means comprising a weakened portion of said second wall means defining an annular segment adjacent said second wall base, whereby said second wall means and the concrete core defined thereby may be separated from the remainder of said sleeve means.

* * * * *